United States Patent [19]

McCormick-Goodhart et al.

[11] 4,404,926

[45] Sep. 20, 1983

[54] APPARATUS FOR RECORDING SURFACE TOPOLOGY

[75] Inventors: Mark H. McCormick-Goodhart, Grosse Pointe Woods; Vincent D. Cannella, Detroit; Robert Minko, East Detroit, all of Mich.

[73] Assignee: Energy Conversion Devices, Inc., Troy, Mich.

[21] Appl. No.: 309,577

[22] Filed: Oct. 8, 1981

Related U.S. Application Data

[60] Division of Ser. No. 937,432, Aug. 21, 1978, which is a continuation-in-part of Ser. No. 890,601, Apr. 14, 1977.

[51] Int. Cl.³ .......................... B05B 5/00; B41K 1/00
[52] U.S. Cl. .................................. 118/641; 118/31.5; 118/102; 346/76 R; 427/1; 427/56.1; 430/346; 430/348
[58] Field of Search ................... 427/1, 56.1; 430/346, 430/348; 118/641, 31.5, 102; 346/76 R

*Primary Examiner*—Bernard D. Pianalto
*Attorney, Agent, or Firm*—Lawrence G. Norris

[57] ABSTRACT

The recording of surface topology is obtained by first bringing the surface into contact with the imaging material-coated side of a dry process dispersion type recording film comprising a transparent substrate on which is coated a very thin, high optical density, opaque body of imaging material, preferably coated with a thin abrasion-resistant protective layer. Radiant energy is then momentarily directed to the imaging material through the transparent substrate. When the heat generated by the absorbed radiant energy is above a given threshold value at a particular location of the imaging material, the material deforms and disperses thereat to form connected or unconnected globules with spaces therebetween. Upon termination of the radiant energy, the dispersed material becomes frozen in place. It was discovered that when a surface having projections and/or depressions, (for example, like that found on the surface of animal or plant tissue) is brought into contact with the recording film as described, at least the projecting portions thereof act as high resolution heat sinks which carry away heat from the imaging material in accordance with the intimacy of contact between the surface involved to be recorded and the side of the recording film contacted thereby, so that heavily heat-sinked points remain opaque and points unengaged by the surface become relatively transparent, to provide a high resolution picture of the surface topology of the contacting body.

15 Claims, 10 Drawing Figures

APPARATUS FOR RECORDING SURFACE TOPOLOGY

RELATED APPLICATIONS

This is a division of application Ser. No. 937,432 filed Aug. 21, 1978 which is a continuation-in-part of application Ser. No. 890,601, filed Apr. 14, 1977.

Also this invention generally relates to a new use of recording films of the type disclosed in (1) application Ser. No. 162,842, filed July 15, 1971, by Robert W. Hallman, Stanford R. Ovshinsky and John P. deNeufville and now abandoned; (2) pending application Ser. No. 577,003, filed May 13, 1975 by Robert W. Hallman, Stanford R. Ovshinsky and John P. deNeufville, as a division and continuation-in-part of said application Ser. No. 162,842; (3) application Ser. No. 407,944 filed Oct. 19, 1973, by Robert W. Hallman, Stanford R. Ovshinsky and John P. deNeufville, as a continuation-in-part of said application Ser. No. 162,842 and now U.S. Pat. No. 4,000,334; (4) pending application Ser. No. 507,049, filed Sept. 18, 1974, by Harvey H. Wacks and Donald J. Sarrach; (5) pending application Ser. No. 725,926, filed Sept. 23, 1976, by Masatsugu Izu and Stanford R. Ovshinsky, now U.S. Pat. No. 4,082,861; and (6) pending application Ser. No. 827,470, filed Aug. 25, 1977, by Masatsugu Izu and Vincent D. Cannella.

Briefly, and generally, the first three of the aforementioned applications, Ser. Nos. 162,842, 577,003 and 407,944, are directed to a dry process recording film utilizing a very thin, solid, high optical density and substantially opaque layer of a dispersion imaging material deposited on a substrate which, upon application of energy like heat energy or radiant energy of at least a given critical or threshold level heat is developed or absorbed in the very thin, but high optical density imaging material which raises the same above its melting temperature which fully disperses and changes the initially continuous imaging layer to one comprising globules and free space or openings therebetween which are frozen in place after termination of such energy and through which free space light can pass for decreasing the optical density thereat, to produce a high contrast film.

The fourth of the aforementioned applications, Ser. No. 507,049, is directed to the imaging system, discussed above in connection with the first three applications, but, in addition, it includes a thin polymeric overcoat layer for protection against abrasion or the like.

The fifth of the aforementioned applications, Ser. No. 725,926, to be U.S. Pat. No. 4,082,861, is directed to the imaging system, discussed above in connection with the first four applications, and is directed generally to two basic improvements therein:

(1) wherein means are associated with the dispersion imaging material for retarding the dispersion and change to the discontinuous state thereof and for controlling the amount of such change in accordance with the intensity of the applied energy above the certain critical value, to increase the amount of such dispersion and change and the area of the openings in the imaging material and decrease the area of globules of the deformed material and, therefore, the optical density of the imaging material in accordance with the intensity of the applied energy above the certain critical value for providing continuous tone imaging of the dry process recording film; and (2) wherein the layer of dispersion imaging material comprises an alloy of a plurality of substantially mutually insoluble solid components having a low melting point eutectic within its system, so that, when energy is applied to the imaging material in an amount to increase the absorbed energy therein above a certain critical value related to the melting point of the eutectic thereof, the imaging material is dispersed and changed, where subject to the energy, to a discontinuous state having the globules of deformed material and the openings or free space which are frozen in place following the application of energy and through which openings or free light can pass for decreasing the optical density of the imaging material thereat with a minimum intensity of applied energy.

The last of the aforementioned applications, namely application Ser. No. 827,490, discloses improved dry process high sensitivity recording films, which can be effectively utilized in a dry process apparatus for producing archival microfilm records and which constitutes a decided improvement over the dry process recording films disclosed in the fifth application.

BACKGROUND OF THE INVENTION

This invention relates to a method and apparatus for recording surface topology on recording films like those disclosed in said applications, the very sensitive continuous tone type of films disclosed in U.S. Pat. No. 4,082,061 and application Ser. No. 827,490 being the films best suited for use in the present invention. The method and apparatus of the invention has its most important present utility in providing excellent quality fingerprints, and records of skin and other tissue surface topology useful in medical diagnosis and research, and for educational purposes where, for example, it is desired to project plant and animal tissue surfaces on a projection screen in a classroom. It also provides surface topology of metals and other materials to detect micro-sized cracks and other surface defects.

The initial surface topology record produced by the invention is a full-sized film transparency record useful immediately as is, or which can be readily projected in magnified form, if desired, onto a screen or photographic film, where almost microscopic details of tissue surface topology becomes readily visible.

Heretofore, the recording of fingerprints has generally been obtained by coating the fingers with ink and then transferring the ink-formed image onto a piece of paper. This is a very messy and inconvenient method of recording fingerprints, and most sophisticated methods and apparatus for recording fingerprints without the use of ink, such as by photographic means, have not heretofore been developed which are sufficiently easy to carry out or use to be feasible for use in police stations and the like.

While various techniques have heretofore been provided for recording the surface topology of skin and other tissue, these methods generally involve taking microscopic pictures of tissue severed from the human body. In such case, recorded images are generally formed on high-resolution silver halide film, requiring a time-consuming developing process which does not make the skin topology involved immediately available to the doctor or researcher. Also, there has not been heretofore developed a convenient method for obtaining the tissue topology of live skin, since it is not feasible to place the particular area of the body involved into the field of a microscope where, to take effective pictures, the skin involved must be pressed against a flat surface to obtain perfectly focused images of the entire skin area involved, while projecting light upon the skin area involved which is necessary to expose the film.

U.S. Pat. No. 3,533,823 to W. H. Newkirk et al discloses a method of making a fingerprint when a finger is pressed upon an imaging material coated on a metal substrate heated to a temperature substantially above room temperature but sufficiently low as not to burn the users fingers. The imaging material is one which has a hysteresis characteristic where the film initially has a very low reflectivity (i.e. black) at room temperature. When elevated above room temperaure it progressively becomes more reflective (e.g. approaching a pure red color). The imaging layer has a given degree of reflectivity prior to the application of a finger thereto. When a finger is placed upon the imaging layer, the points thereof contacted by the ridges of the finger cool the same so that these portions of the imaging layer will have a different degree of reflectivity. When the finger is removed from the imaging layer, the portions thereof previously cooled are heated to the same temperature as the rest of the same. However, because of the hysteresis effect of the imaging layer the degree of reflectivity of the previously cooled portions of the imaging layer will be different from those not originally contacted by the ridges of the finger. The pattern of the ridges of the user's finger will, therefore, be present on the imaging layer until the temperature of the imaging layer is lowered to room temperature where all color differentiation therein disappears. A photograph of the original imprint must thus be taken to obtain a permanent record of the fingerprint. The requirement of a camera as part of the process of providing a permanent record of a fingerprint makes the process involved a very unwieldly one. The only advantage of this process over fingerprinting process utilized prior thereto is that it avoids the necessity of using messy fingerprint ink.

U.S. Pat. No. 3,070,428 to Cohen discloses a process for reproducing negative images of the raised portion of metal surfaces applied to the imaging layers of Thermofax papers or transparencies which must be bulk-heated to substantially elevated temperatures as disclosed in this patent. These temperatures fall in the range of from about 50° to 250° C. and the heat is applied for as short a period as 0.1 seconds and for as long as 60 seconds. The specific examples given in the patent specify 5 or more seconds of heat application to achieve the desired results. The areas of the Thermofax paper engaged by the raised portions of a metal surface are cooled thereby, so that these portions thereof are not affected by the heat, whereas those portions thereof not contacted by the metal surface are heat-imaged to a dark color, black in the example given in the patent.

The process for reproducing negative images of metal surfaces disclosed in this Cohen patent are manifestly not suitable for making fingerprints. Thus, the necessity for bulk heating the substrate of the papers requires heat application times to raise the temperature of the paper to the high imaging temperatures that would cause a serious risk of burning a user's finger should the process disclosed be used to obtain fingerprints. One reading this patent would not, therefore, think of applying the process thereof to obtaining fingerprints.

One further serious disadvantage of utilizing Thermofax papers and transparencies to provide an image of even a metal surface topology is that the images produced are damaged or destroyed by heat and readily deteriorate. Therefore, such papers do not have the desired archival properties for many applications like fingerprint records for police files.

It is, accordingly, an object of the invention to provide a process and apparatus for recording details of surface topology of various surfaces, including live skin and other tissues, which do not require camera equipment or the application of any ink or other imaging materials to the surface involved. Another object of the invention is to provide a method and apparatus as described wherein the application of the surface to be recorded to a recording film produces an immediate image, preferably an image transparency, which can be readily projected by conventional transparency projection equipment.

A further object of the invention is to provide a method and apparatus as just described which does not require the external heating of the imaging film involved, so that no problems of burning or discomfort to live skin tissue is possible.

A still further object of the invention is to provide a method and apparatus as described which produces a record of said surface topologies immediately upon exposure of the recording medium to radiant energy, like an Xenon flash unit or the like, and without using any chemicals or other consumable materials.

Another object of the invention is to provide a method and apparatus as described which produces a permanent image having such archival properties that no special temperature or humidity conditions are required for the storage thereof.

Still another object of the invention is to provide a method and apparatus as described which has such a high degree of resolution that details which are clearly recorded are as small as about 3-5 micron in size.

A further object of the invention is to provide a method and apparatus as described where unskilled personnel can be used to practice the method or operate the apparatus thereof.

DESCRIPTION OF THE INVENTION

The present invention resulted from a discovery that when the ball of a finger was brought against the imaging material coated side of a dispersion recording film like those disclosed in said applications and a flash of radiant energy of a Xenon flash lamp lasting for a small fraction of a second like that commonly used in taking flash photographs (i.e. typically no greater than about 1/1000 second) was applied through the transparent, substrate side of the film during only the period when the finger contacted the film, there was produced an extremely clear transparency fingerprint record where the depressions in the finger surface appeared in the transparent imaged portions of the film and at least the peak portions of the surface appeared in the relatively opaque portions of the film. When the fingerprint was projected in greatly magnified form on a screen or photographic film subsequently developed, microscopically small details, like pores and other minute depressions, become clearly visible. Moreover when a continuous tone form of dispersion type film is used, a degree of transparency is produced in the portions of the film confronted by the various portions of the finger in accordance with the intimacy of contact between the various points of the finger surface involved and the recording film, which produces a three-dimensional visual effect. Similar results are achieved when exposing the recording film as described, while pressing other areas of the skin or other tissue, or surfaces of various objects against the imaging layer coated side of the recording film. These films have archival properties and do not require any special storage conditions.

These surprising results are believed to result from the construction and characteristics of the film involved and the unique relationships between the tissue or object surface, radiant energy and the recording film. (Normally, such films are exposed from their imaging layer coated rather than their substrate side.) The dispersion recording films described have a thin protective layer (e.g., 0.5 micron thick) overlying a very thin body of imaging material (e.g., 0.05 micron thick) of a high optical density. As previously explained, this opaque imaging material absorbs very efficiently the electromagnetic energy of the flash lamp, the absorbed energy generating heat within the material which, in the absence of a heat-sinking surface contacting the recording film, raises the temperature of all energy exposed portions thereof to a threshold temperature causing deformation and dispersal of the imaging material. This dispersion of the imaging material becomes frozen into such condition when the radiant energy terminates, to produce openings in the initially continuous imaging material. In the preferred continuous tone type of film, the degree of which such dispersion takes place and the resulting ratio of globules to free space therebetween at a given film location and, therefore, the degree of transparency produced thereat decreases with an increase in the amount of heat dissipated through each surface location of the confronting body.

It should be noted that with the dispersion films described, if the source of electromagnetic energy is continuously applied to the recording film after removal of the imaging surface therefrom, the continuous application of electromagnetic energy would then also raise the portions of the film previously heat-sinked to a point below the threshold temperature of the imaging layer to the threshold value, so that the image produced would be destroyed. Thus, the electromagnetic energy must be applied to the recording film only during the period when the surface to be imaged remains in contact with the recording film.

Of great importance is the fact that the invention does not raise any risk of discomfort or harm to live skin tissue since the electromagnetic energy from the flash lamp applied for a very small fraction of a second does not develop a sufficient quantity of heat energy in the imaging layer as to create any discomfort in the user's skin whatsoever. It is well known that certain portions of the human body are more sensitive to heat than others. For example, the skin tissue on the wrist is much more sensitive to heat than is the much thicker skin of the fingers. It was found, therefore, that using a conventional Xenon flash lamp which generates radiant energy of the order of magnitude from about 0.6 to 1.0 Joules/cm$^2$ and a flash duration of the order of magnitude of 1/1000 second will not generate sufficient heat as to cause any discomfort when a person's finger is imaged by the present invention. However, some sensation (but no burning) may in some cases be felt with such a flash duration if an image is taken of the skin tissue of the wrist. Therefore, while a flash duration of 1/1000 second is usable in the invention to form images of live skin tissue of human beings in the most preferred form of the invention where it is desired to provide a method and apparatus which can be used to take the images of skin tissue of any portion of the body it is preferred that the flash duration be an order of magnitude smaller than 1/1000 second, that is no greater than about 1/10,000 second. An additional advantage of such very short flash times used in the present invention is that short flash times produce higher resolution images in the dispersion films described than longer flash times. A prolongation of the flash times to an order of magnitude, for example, of 1/100 second would seriously adversely affect the image resolution produced in the dispersion films disclosed herein. Thus, shorter flash times are desirable both from the standpoint of eliminating discomfort to the person whose skin image is being obtained and also to maximize the resolution or clarity of the image produced. The former advantage, however, is of much greater importance than the latter, for most skin imaging purposes.

The fact that the raised portions of an imaging surface making good contact with the imaging material coated side of a dispersion recording film can have an effective heat-sinking effect is highly unexpected. Thus, the previously known heat-sinking effects on recording films involve an environment where external heat is applied to the substrate side of the film so that the surface which contacts the imaging layer-coated side of the film would draw away heat directed to the imaging layer from the substrate. In the present invention, the heat-sinking effect is operative upon heat initially generated in the imaging layer by electromagnetic energy directed thereto. Also, it is unexpected that the portions of the imaging surface contacting the imaging layer-coated side of the recording film would have an effective heat-sinking effect on a source of heat produced by a pulse of energy of only a small fraction of a second duration. Perhaps one of the reasons the film-contacting portions of the imaging surface have a heat-sinking effect on dispersion films even when the energy source occurs during only such a short interval of time is that the dynamics of the dispersion of the imaging layer is such that the dispersion takes place for a period after the cessation of the application of the source of electromagnetic energy and the heat-sinking effect of the contacting imaging surface remains effective after the termination of the electromagnetic energy. Additionally, it would not appear feasible that a desirably sharp image could be produced by variable heat sinking effects through a protective layer between the imaging layer and the point of contact of the imaging surface with the recording film which is several times thicker than the imaging layer because the protective layer would spread the heat-sinking effect and adversely effect the image resolution obtainable. However, the protective layer used in the recording films described is so thin (that is, under one micron) that the resolution expected, namely the order of magnitude of the thickness of such protective layer, is still quite effective in bringing out such minute details as ridges and pores of skin tissue.

It should also be noted that in the most preferred form of the invention the time duration of the electromagnetic energy is no greater than about 1/1000 second (a period which insures that the image produced will not be blurred even if there should be a small amount of movement of the finger when applied to the recording film). Such an unblurred result is not readily possible, for example, in the case where a pulse of heat is applied to the recording film lasting at least several seconds, during which time the imaging surface must be applied to the recording film to have its desired heat-sinking effect, as in the case of the process disclosed in said Cohen patent.

The present invention provides the most effective results, whether using a continuous tone or a high contrast recording film, when the surface to be recorded is that of a soft, pliable body like skin tissue. In such case, when the body is pressed against the recording film the area and intimacy of contact of the body surface increases with the pressure between the contacting body and the recording film. The heat-sinking effect of such a body and the clarity and resolution of the recorded image can be readily optimized. Additionally, the amount of heat dissipated through such a contacting body varies with the pressure applied to the various points of the surface engaging the recording film. Thus, the pressure at the peaks of the protrusions of a contacting body which are pressed against the recording film and which make the initial contact with the recording film will be greater than the pressure at the points of the contacting body adjacent to these peaks of the protrusions, so that there will be gradation of pressure applied to the various points of such a contacting body. The heat conductivity of the various points of such a contacting body engaging the recording film will vary with the pressure applied thereto, so that forming an image of the surface of such a contacting body on a continuous tone recording film will produce a gradation of opacity and transparency and a three-dimensional effect therein. Also, the depressions of the body surface will have a similar variable heat-sinking effect depending upon the depth of the depressions at each point of the contacting body.

Some difficulty is usually encountered in producing good surface topology images of rigid surfaces, like the surfaces of metal objects in which surface cracks or defects are to be detected by the present invention. Since most metal surfaces comprise rough surfaces at the microscopic level, it is difficult to provide an intimacy of contact which will bring out clearly surface details produced by soft pliable bodies. Thus, metal surfaces may not contact the recording film except at relatively widely spaced points, so that the spaced between these contact points which do not produce heat-sinking effects appear as blank or transparent areas in the imaged recording film, and so surface cracks and the like do not appear in the image produced. However, by applying a thin layer of a heat-transmitting material, such as a suitable liquid or grease of a proper thickness, various portions of such a surface between the contacting peaks of the metal surface can be made to have an effective variable heat-sinking effect on the recording film which can bring out surface defects. Another means for bringing out the surface topology of the surfaces of hard objects is to make the substrate and the other layers of the recording film of a very pliable and deformable material, which can follow minute variations in the elevation of the rigid surface areas of the body involved.

Normally, the dispersion type film described is exposed through an image-producing mask or by projecting a full format image onto the imaging layer coated side of the recording film. However, the recording process described exposes the imaging material through the transparent substrate, while the surface to be recorded is pressed against the other side of the recording film (which is separated from the exposed substrate by the initially continuous opaque imaging material). The above described progressive, high resolution, differential heat-sinking effect produced by the various projecting and/or recessed portions of the surface to be recorded probably could not be achieved very effectively if the surface was, for example, spaced from the imaging material by a relatively large distance or if the imaging material was very thick. This is because thicker films have a high heat retention capacity so that a contacting surface will have a relatively smaller heat-sinking effect thereon. Also, a larger spacing between the contacting surface and the imaging material reduces the high resolution effect of the heat-sinking produced by the contacting surface. Most heat-responsive recording mediums in use today are not very sensitive to radiant energy, and have usually lightly colored or transparent imaging layers coated on paper or transparent substrates, which imaging layers produce relatively dark visible images when subjected to externally applied heat energy. The differential heat sinking effect of a contacting surface would not produce the results of the present invention when applied to these initially wholly transparent recording films or initially opaque recording papers when exposed to radiant energy from the substrate side, because these recording films do not have a very efficient radiant energy-absorbing imaging layer and/or because the substrate is opaque. Thus, if a given surface pressed against the imaging material coated side of the film is to have its high resolution heat sinking effect on the heat produced in the imaging material maximized when the radiant energy is directed from the substrate side of the recording film, the substrate should be transparent to the radiant energy, and the imaging material most preferably should be a very thin high optical density material.

Since the dry process dispersion-type film described produces an image immediately upon being exposed to the flash lamp energy, an accurate record of the surface topology involved becomes immediately available, without the necessity of using chemicals to form an image, which makes the invention usable by unskilled personnel and in the manufacture of uncomplicated apparatus for carrying out the method aspects of the invention. Thus, fingerprinting apparatus useful in police stations and the like, and tissue topology recording apparatus useful in hospitals and doctor's offices and in educational institutions, which carry out the method aspects of the invention can be manufactured at very low cost. Such apparatus could comprise a housing with a raised, upwardly spring-urged transparent recording film-receiving platform connected to a pressure-responsive control switch or the like. A record of the tissue surface topology would be made by pressing the fingers or other tissue involved upon the imaging material coated side of a dispersion recording film extending over the film-receiving platform. When the pressure on the platform reaches an optimum value, the pressure-responsive control switch operates to momentarily energize a flash lamp which directs light through the platform and substrate side of the recording film which immediately provides a clear image of the surface topology of the tissue involved. Back-lighting the film then makes the image involved clearly visible. Where the recording film is wound on a roll and extends between supply and take-up spools in this apparatus, upon exposing the recording film, the newly exposed portion of the film can be automatically advanced to a back-lighted projection station where the surface topology record of the tissue involved can be examined immediately to determine if the record made is satisfactory and to examine the surface topole of the tissue involved.

The above and other objects, advantages, and features of the invention will become apparent upon reference to the specification to follow, the claims, and the drawings.

DESCRIPTION OF EXEMPLARY EMBODIMENTS OF THE INVENTION

Figure 1:
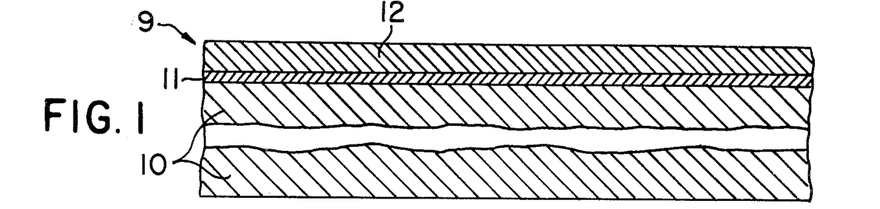
FIG. 1 is a greatly magnified sectional view through a recording film useful in the present invention.
Figure 2:
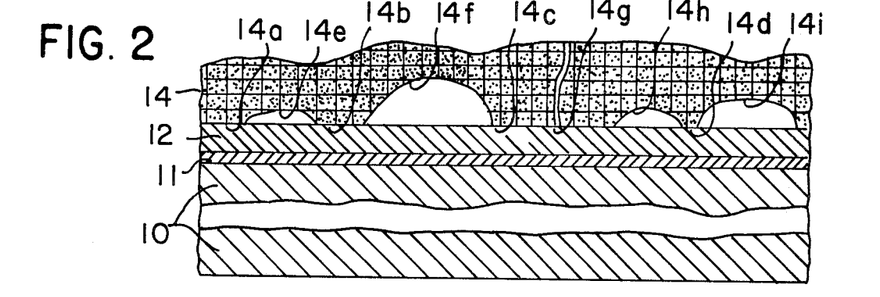
FIG. 2 is a cross-sectional view of the recording film shown in FIG. 1 after a skin surface, like the ball of a finger, has been placed upon the imaging material-coated side of the recording film.
Figure 3:
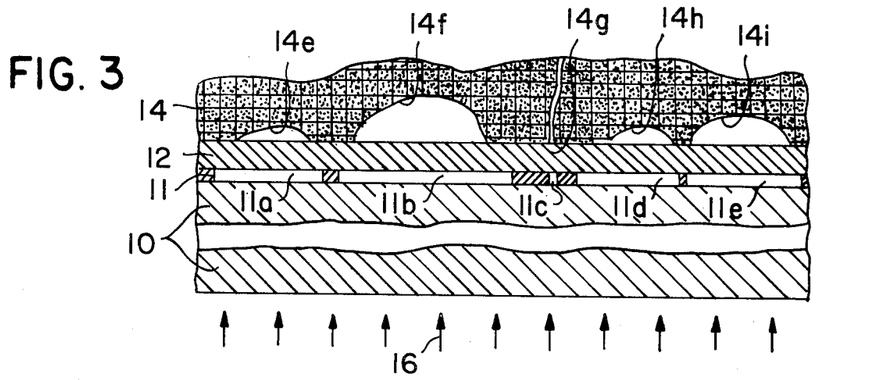
FIG. 3 shows the development of discontinuities or openings in the initially continuous imaging material of the recording film when a flash of radiant energy has been directed through the transparent substrate of the recording film shown in FIG. 2 onto the imaging material of the recording film.

Referring first to FIGS. 1 through 3 showing one form of a high sensitivity recording film generally designated at 9 useful in the present invention. It includes a transparent substrate 10, and while it may be formed from substantially any substrate material, it is preferably formed from a polyester material, such as a polyethylene terephtalate, known as Melinex type 0 microfilm grade, manufactured and sold by ICI of America. The thickness of the substrate 10 is preferably in the range of from about 2 to 7 mils, most preferably from 3 to 5 mils. Deposited on the substrate 10, as by vacuum deposition or the like, is a thin continuous body 11 of dispersion imaging material which may comprise one or different layers or films of materials. The thickness of the body 11 of dispersion imaging material is such as to provide an optical density of about 1.0 to 2.5. Generally, the thickness of the body 11 of imaging material will run about 0.01 to 0.1 micron, preferably about 0.05 micron. The thin body 11 of dispersion imaging material is one which absorbs radiant energy produced, for example, by a flash lamp which becomes converted, at least in part, to heat energy which can raise the temperature thereof to one where the material disperses to form a discontinuous film which allows light to pass through the material. While not shown in FIGS. 1 through 3, to assure that moisture and oxygen do not gain access to the body 11 of imaging material, a thin transparent layer of a sealing material (e.g., 0.02 micron thick, referred to as a passivation layer) may be interposed between the body 11 of imaging material and the underlying substrate and between the body 11 and a substantially transparent protective overcoat layer 12. The overcoat layer may have a thickness range of about 0.1 to 10 microns and is preferably no greater than about 1 micron and most advantageously about 0.5 microns thick for highest resolution. It is preferably formed of a suitable polymer resin, as for example, polyurethane estane No. 5715 as manufactured and sold by B. F. Goodrich Co., or silicon resin, Dow Corning R-4-3117 as manufactured and sold by Dow Corning Co., or polyvinylidine chloride (Saran) as manufactured and sold by Dow Chemical Co. The overcoat film may also comprise a photoresist material such as polyvinylcinnamate, for example, a Kodak KPR-4 photoresist manufactured and sold by Eastman-Kodak Co. The overcoat film may be applied by spin coating, roller coating, spraying, or the like.

If a passivating layer is utilized on each side of the body 11 of imaging material, it may be deposited as by vacuum deposition on the substrate before the body 11 of dispersion imaging film is deposited thereon and the other passivating layer may be deposited in the same way on the body 11 of dispersion imaging film before the protective layer overcoat 12 is deposited thereon. The passivating layers may comprise SiO, $SiO_2$, $Al_2O_3$, $GeO_2$, $B_2O_3$, $Bi_2O_3$ or the like or various combinations thereof. The passivating layers, by preventing or limiting oxidation of the body 11 of dispersion imaging material, avoids possible deterioration of the optical density thereof over a period of time. These passivating layers, as expressed above, also effect the interfacial adhesion between the substrate and the body 11 of imaging material and between the overcoat layer 12. The passivating layers preferably each have a thickness of about 0.006 to 0.05 micro and more preferably between 0.01 and 0.03 micron.

FIG. 2 illustrates a cross-sectional view of the recording film 9 shown in FIG. 1 after a skin tissue 14, which may be the ball of a finger, is pressed against the protective overcoat layer 12. This skin tissue is shown as having projecting portions 14a, 14b, 14c, etc. between which there are shown recesses or depressions 14e, 14f, 14g, 14h, etc. The recesses have varying depths as shown, and the recess 14g is a pore in the skin tissue. In FIG. 2, the body 11 of imaging material is still a continuous, highly opaque body. Referring now more particularly to FIG. 3, when a flash of radiant energy (represented by reference numeral 16) of a value, for example, commonly produced by commercial Xenon flash lamps, is directed through the substrate side of the recording film 9, the body 11 of imaging material will absorb this energy and convert the same to heat energy. It was discovered that heat energy, which heretofore was sufficient to cause the body of a dispersion imaging material to disperse to form openings or discontinuities therein, did not have any or the same material-dispersing effect in the areas or regions of the recording film (whether it was a high contrast or continuous tone recording film contacted by the initially peak portions of the skin tissue. On the other hand, in those areas or regions of the skin tissue where the recesses or depressions 14e, 14f, 14g, etc. were located, the body of imaging material dispersed in the expected way, to provide transparent areas 11a, 11b, 11c, 11d and 11e immediately opposite the recesses or depressions 14e, 14f, 14h and 14i. There was therefore, produced an image approximating the surface topology of the skin tissue surface pressed against the protective layer 12 of the recording film 9.

In a high contrast dispersion film each of the transparent areas 11a, 11b, 11c, and 11d and 11e have the same degree of transparency and, when viewed microscopically, comprise spaced globule of the imaging material with a constant ratio of globules to free space. In an image continuous tone film the ratio of globules to free space therebetween of the transparent areas 11a, 11b, 11c 11d and 11e varies with the intimacy of contact or pressure on the various sections of each projecting portion 14a, 14b, etc. of the tissue surface and the depth of the various sections of each depression or recess 14e, 14f, etc. thereof. Since the body 11 of imaging material is not affected by the heat generated therein until a given threshold level or critical value of undissipated heat is generated therein, the intensity of the radiant energy source should be sufficient to raise the unheat-sinked areas of the recording film above the dispersing temperature thereof, but insufficient to raise the most heavily heat-sinked areas of the recording film to the dispersing temperature thereof. The utilization of a continuous tone type of dispersion film where a gradation in the degree of transparency is produced in accordance with the degree of heat sinking produced at the interface between the recording film and the surface involved, will generally give more information on the surface topology of a contacting body than will a high contrast dispersion film.

Figure 4:
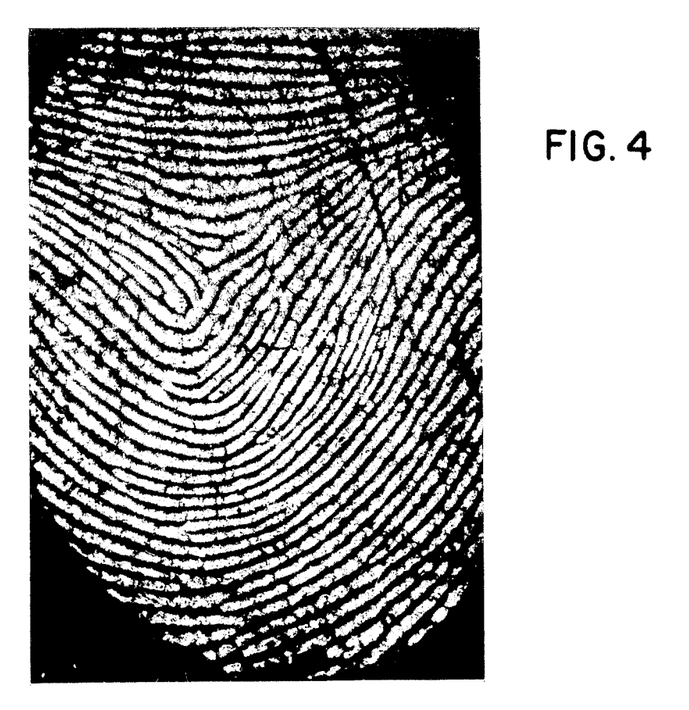
FIG. 4 is a photographic print of a fingerprint enlarged directly from a transparency formed by the recording film of FIG. 7 utilizing the process of the present invention.
Figure 5:
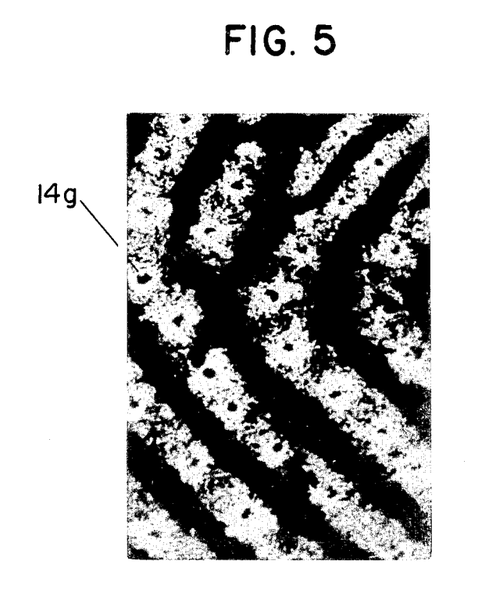
FIG. 5 is a photographic print of a more greatly enlarged image of a portion of the fingerprint image shown in FIG. 4, also enlarged directly from a transparency formed by the recording film of FIG. 7 utilizing the process of the present invention, and illustrates the image resolution produced by the present invention, where individual pores are clearly visible thereon.
Figure 6:
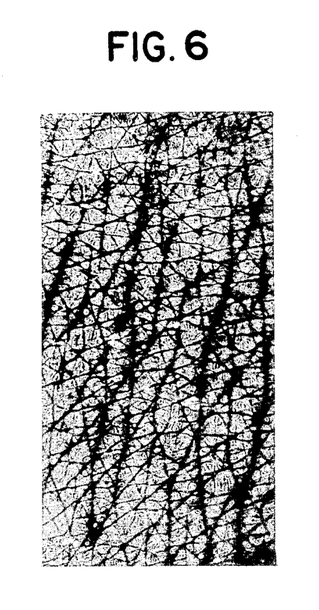
FIG. 6 is a photographic print of an arm skin tissue image enlarged directly from a transparency formed by the recording film of FIG. 7 utilizing the process of the present invention.

Refer now more particularly to FIGS. 4 and 5, FIG. 5 being a magnification of a portion of FIG. 4, which are photographic prints of a fingerprint enlarged directly from the transparency formed by the present invention when a dispersion recording film used. In these photographs, the projecting portions of the skin tissue 14 involved are shown as light areas and the recesses or depressions are shown as dark areas. These images were produced on a continuous tone-type of film where the degree of darkness of the image varies from gray to black to give a three-dimensional effect FIG. 5 shows the pores of 14g as black dots, attesting to the finish resolution produced by the recording process of the present invention. Also exemplary of these results is FIG. 6, which shows a photographic print enlarged directly from the transparency formed by the present invention when a portion of the arm was pressed against the protective layer 12 of recording film 9. The surface topology images shown in FIGS. 4 through 6 were produced on a recording film like that shown in FIG. 7 to be described where the Xenon flash lamp radiant energy fell in the range of from about 0.6 to 1.0 Joules/cm$^2$ with a flash duration between about $10^{-3}$ to $10^{-5}$ seconds.

The body 11 of imaging material, whether it be a high contrast or continuous tone film, as disclosed in said first four mentioned patent applications may comprise a single layer of alloy material which is substantially homogeneous or uniform throughout the alloy layer, but which is microheterogeneous with respect to the substantially mutually insoluble solid components thereof and which has a eutectic mixture as disclosed in said aforementioned fifth application. This application also discloses and contemplates the simultaneous deposition of the substantially mutually insoluble components of the alloy in a single deposition step to achieve the substantially homogeneous or uniform single alloy layer.

In the most advantageous form of recording film disclosed in said application Ser. No. 827,470, the body of dispersion imaging material deposited on the substrate includes a plurality of separate overlying layers 11a, 11b and 11c (FIG. 7) of different and substantially mutually insoluble components having relatively high melting points and relatively low melting point eutectics, and interfaces between said layers having relatively low melting points. The relatively low melting points of the interfaces between the separate layers correspond generally to the relatively low melting point eutectic of the components of the separate layers. Passivating layers 16 and 18 are respectively deposited on the substrate 10 and on the body 11 of imaging material and an overcoat layer 12 is preferably deposited on the outer surface of the film.

Electromagnetic energy like Xenon flash lamp energy is applied to such body of dispersion imaging material in an amount where the undissipated heat energy produced thereby will increase above a certain critical value to increase the temperature thereof to the relatively low melting points of the film interfaces, to substantially melt the low melting point interfaces and incorporate the different and substantially mutually insoluble components of the separate layers into the substantially molten interfaces and, hence, to change the imaging material to a substantially fluid state in which the surface tension of the material acts to cause the substantially opaque material, where subject to said energy, to disperse and change to a discontinuous material comprising openings and deformed material which are frozen in place following the application of energy and through which openings light can pass for decreasing the optical density thereat.

The deposited separate layers of the different and substantially insoluble components like bismuth and tin having relatively high melting points (278° C. and 232° C., respectively) have low melting point interfaces due to the energy of mixing of the separate components at the interfaces thereof, or which may comprise a layer of a eutectic mixture of the separate components which layer may be microscopically thin. The application of the electromagnetic radiant energy above the certain critical value causes the components at the layer interfaces to substantially melt and to cause the components of the separate layers to be broken up and at least substantial amounts thereof to be incorporated in the melt. As a result, the solid continuous body of imaging material, including the separate layers, is changed to a substantially fluid state wherein the surface tension thereof causes the material to disperse and change to a discontinuous body. Due to the low melting points, this occurs at a low intensity of the applied energy and, therefore, provides a high sensitivity recording film.

By utilizing a plurality of separate layers of different and substantially mutually insoluble components like bismuth and tin having relatively low melting point eutectics and relatively low melting point interfaces therebetween, as aforesaid, numerous improvements and advantages are brought about. Among others, the need for providing a substantially homogeneous or uniform layer of a deposited alloy and the difficulties involved in doing so are eliminated. The difficulties in controlling the relative amounts of the components making up such a deposited alloy layer are also eliminated. Appropriate components for the respective layers may be selected and readily and simply deposited on the substrate in desired amounts and in desired orders for providing the body of dispersion imaging material with desired characteristics, as for example, the melting points of the low melting point interfaces between the layers, the intensity of the heat energy absorbed thereby to disperse and change the continuous body of dispersion imaging material to a discontinuous one.

The gammas of these films have been found to be a function of several parameters which can be controlled. Briefly, among these parameters are: the relative thickness of each component layer of the body of imaging material; the density of roll back nucleation points as well as impediments to roll back provided by both cumulative crystal structure, solids, and impurities introduced into the component films; the combined thermal properties of the component layers, substrate, overcoat and other layers; and the crystal grain size and orientation in the component layers.

In the continuous tone imaging films having a low gamma, the parameters are such as to provide means associated with the body of dispersion imaging material for retarding the dispersion thereof and the change to a discontinuous body, caused by the surface tension, and for controlling the amount of such dispersion and change in accordance with the intensity of the applied energy above said certain critical value to increase the amount of said change and the area of the openings in the body of imaging material and to decrease the area of the deformed material in the body and, therefore, the optical density of the body in accordance with the intensity of the applied energy above said critical value, for providing continuous tone or gray scale imaging of the dry-process recording film. In this respect, the retarding and controlling means associated with the body of dispersion imaging material retards the roll back of the deformed material from the initial openings in the body and controls the amount of such roll back of the deformed material in accordance with the intensity of the applied energy above said certain critical value.

Figure 7:
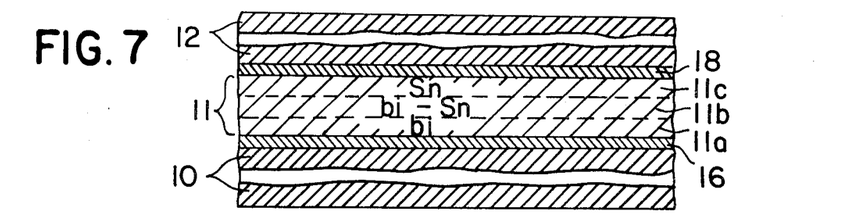
FIG. 7 is a further magnified sectional view of one exemplary form of the recording film shown in FIGS. 1 through 3, showing various regions or layers of the film not visible or shown in FIGS. 1 through 3.

The various layers of the body 11 of dispersion imaging material of FIG. 7 and also the passivating layers may be deposited on the substrate in various ways, as for example, among others, by vacuum deposition, including resistance heating or electron beam deposition or the like. In the case of resistance heating vacuum deposition, a vacuum chamber may be utilized and may have a copper substage holder for holding the substrate of the film. Located below the film substrate held by the copper substage is a plurality of resistance heated boats made of tungsten, molybdenum, tantalum or the like, depending upon the materials to be evaporated therefrom. These resistance heated boats are arranged side by side in close proximity and about 6 to 9 inches below the film substrate. A clean glass chimney is preferably arranged between the film substrate and the boats in the deposition system to prevent contamination of the rest of the system by the materials evaporated from the boats. The copper substage is preferably maintained at about room temperature. The materials to be evaporated are separately placed in the different resistance heated boats, as for example, bismuth, tin and the like, and also the materials for the passivating layers, if utilized.

The vacuum in the vacuum chamber is pulled down to about 1 to $5 \times 10^{-6}$ Torr, which operates first to outgas the polyester substrate held by the copper substage. The layers of the components forming the layered dispersion imaging material and the passivating layers, if utilized, are deposited successively on the substrate to desired thicknesses from the different resistance heated boats by successively heating the same to vapor deposition temperatures. The depositions of the various layers are done with out breaking the vacuum in the vacuum chamber. The completed film is then removed from the vacuum chamber and immediately coated with the polymer overcoat as by spin coating, roller coating, spraying or the like. The vacuum deposition of the various layers are controlled to provide desired layer thickness. If a high contrast film is to be made, no oxygen is introduced into the vacuum chamber during deposition, so that substantially no oxides are introduced into the imaging film. If a continuous tone film is desired, oxygen is introduced into the chamber.

The depositions of the layers by the electron beam vacuum deposition procedure may be done in a continuous web process. This process utilizes a vacuum chamber having therein a web payoff spool, a water cooled drum and a web takeup spool with the polyester substrate coursing the same. A web position idler is preferably arranged between the water cooled drum and the web takeup spool. The system also includes a multiple boat turret electron beam gun wherein the multiple boats respectively have different materials therein to be evaporated by the electron beam gun. The turret electron beam gun is arranged below the water cooled drum at a distance of about 10 inches. The multiple boats in the turret are selectively moved with respect to the electron beam gun so that the materials in the boats may be selectively evaporated by the electron beam and deposited on the substrate as it is passed over the water cooled drum. The system also includes a crystal rate controller which electronically controls the deposition power of the electron beam gun. The system may further include an optical monitor for monitoring the depositions of the respective layer materials on the substrate as to optical density.

The various bismuth and tin layers 11a, 11b, 11c(FIG. 7) may be deposited in sequence during a single pass of the web. Here, the deposition apparatus may include the same apparatus described immediately above. It may also utilize a resistance heated boat arranged laterally and upwardly from the turret boats of the electron beam gun toward the payoff spool side. The resistance heated boat is located about 6 inches below the water cooled drum and a baffle extending below and upwardly along the side of the resistan heated boat operates to guide the deposition streams from the resistance heated boat and from the turret electron beam gun onto the web coursing the water cooled drum. In this respect, the deposition stream from the resistance heated boat, for example, bismuth, is first deposited on the web to provide the layer 11a and then the deposition stream from the turret electron beam gun, for example, tin, is next deposited, with some partial overlapping of the deposition streams depending upon the guiding action of the baffle to provide the intermediate layer 11b, with the layer 11c provided by the unoverlapped portion of the tin stream. By raising the baffle the intermixing or overlapping is decreased and by lowering it the mixing or overlapping is increased and, thus, the structure of the interface between the layers may be controlled as to the amount of eutectic mixture therein and the gradation thereof.

A specific example of this last mentioned vacuum deposition procedure used to produce a continuous tone recording film comprises pulling down the vacuum chamber to less than about $5 \times 10^{-5}$ Torr and paying the substrate off the payoff spool over the water cooled drum to the takeup spool, and reversing the substrate back onto the payoff spool at a speed of about 3 ft/min for the purpose of outgassing the substrate. The substrate is then advanced from the payoff spool and has deposited thereon a first passivation layer of about 150 Å of $GeO_2$ deposited from one of the turret boats by the electron beam at a rate of about 20 Å/sec and a web speed of about 3 ft/min. The deposition rate is controlled by using the crystal rate controller which electronically controls the deposition power of the electron beam gun. The coated substrate is then returned to the web payoff spool for the next deposition step. Oxygen is then bled into the vacuum chamber through a needle valve while pumping a vacuum to establish a dynamic steady state pressure of $O_2$ in the system. A pressure of about 1 to $2 \times 10^{-4}$ Torr of $O_2$ is maintained and the coated substrate is advanced from the payoff spool at a speed of about 1 to 3 ft/min. The resistance heated boat is energized to deposit bismuth onto the coated substrate to an optical density of about 0.7 when the coated substrate is moved at the aforementioned speed. The deposition of the tin from another boat of the turret electron beam gun is made at a rate adjusted to give a total optical density to the film of about 1.4. Thus, bismuth is first deposited on the coated substrate followed by the sequential deposition of tin thereover to provide layers of bismuth and tin with a mixture thereof therebetween to a total thickness of about 250 Å providing a total optical density of about 1.4. The tin deposition rate was typically about 40 to 60 Å/sec.

Following this sequential deposition of bismuth and tin, the coated substrate with the bismuth and tin sequentially deposited thereon is returned from the takeup spool to the payoff spool and the flow of $O_2$ into the vacuum chamber is stopped and the residual oxygen pressure is evacuated. Thereafter, the film is advanced from the payoff spool to the takeup spool and a passivation layer of $GeO_2$ is deposited thereover from the first boat in the turret electron beam gun to a thickness of about 150 Å. The web is then removed from the vacuum chamber and is roller coated with a polymer overcoat having a thickness of about 6000 Å. Care is taken in the payoff and takeup spools, both during evaporation depositions and polymer coating to control the web tension to avoid scratching, telescoping and so forth of the imaging film.

Figure 8:
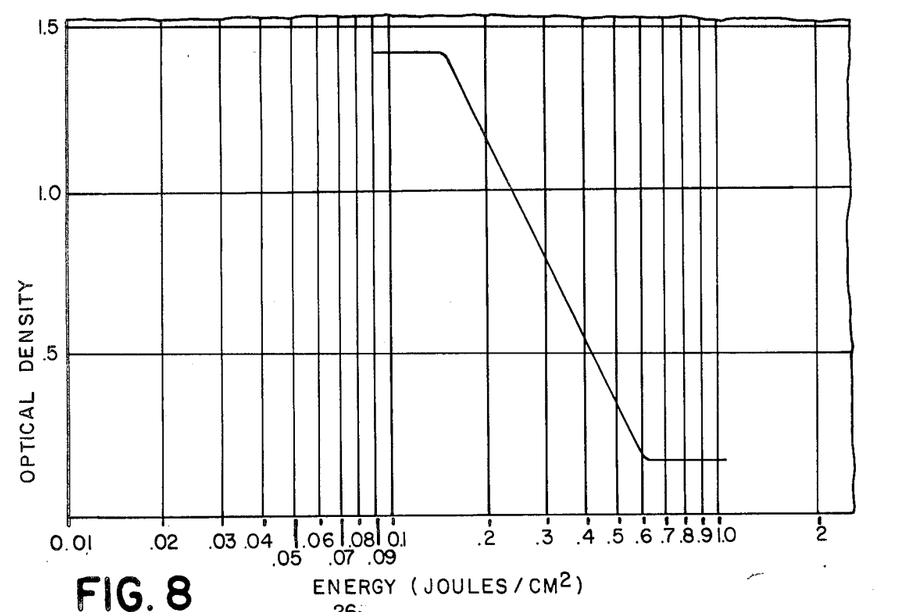
FIG. 8 is a graph showing the variation in optical density of the film shown in FIG. 7 under various radiant energy intensities applied to the film in the absence of any skin tissue or other surface applied to the imaging material-coated side of the recording film.

The introduction of oxygen into the vacuum chamber during the sequential deposition of the bismuth and tin produces oxides therein which operate to provide a continuous tone imaging film having relatively low gamma corresponding generally to the curve 42 in FIG. 8. By controlling the amount of oxygen fed into the vacuum chamber during the sequential deposition of the bismuth an tin, the gamma of the imaging film may be controlled, the more th oxygen introduced into the vacuum chamber, the more are the oxide incorporated in the film and the lower the gamma of the film.

Figures 9, 10:
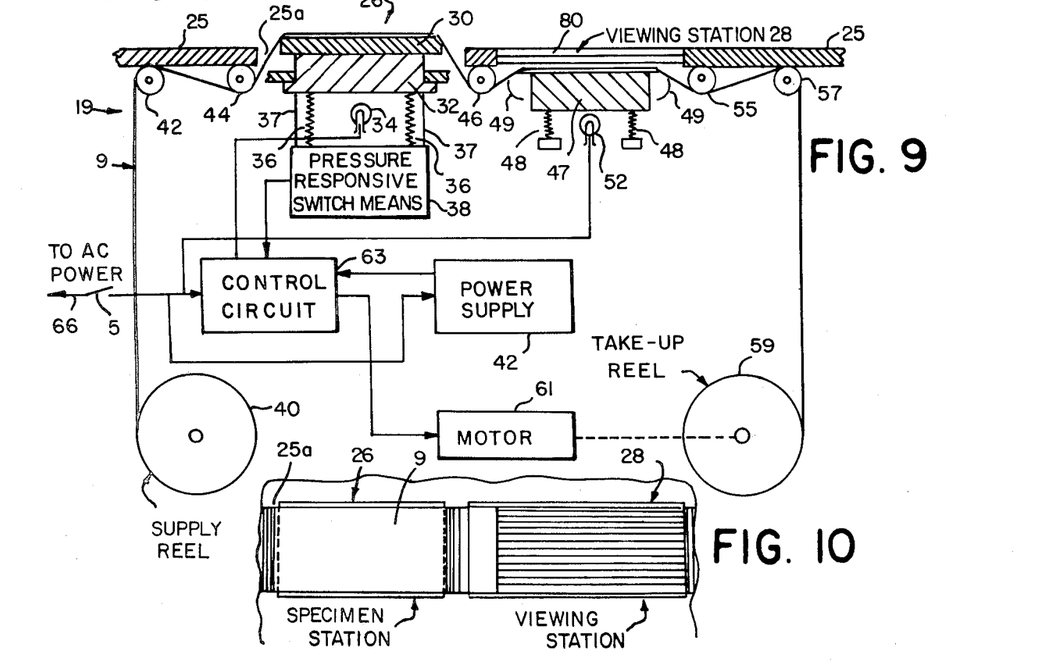
FIG. 9 is a diagrammatic fragmentary view of a fingerprint machine which utilizes the features of the present invention.
FIG. 10 is a plan view of the specimen-receiving and viewing stations of the machine shown in FIG. 9.

Reference should now be made to FIGS. 9 and 10, which show an example of a machine for recording and displaying the surface topology of skin and other tissue in accordance with apparatus features of the invention. As there shown, projecting upwardly through an aperture 25a in the housing 25 of the apparatus is a specimen-receiving station 26 comprising a transparent raised platform 30 made of glass or a synthetic plastic material secured to a quartz light-dispersing block 32 spring-urged upwardly by springs 36—36 to an uppermost position. Recording film 9 is shown in the form of an elongated strip of film passing out of the housing 25 through an aperture 25a and extending over the top surface of the platform 30. Xenon flash lamps 34 are mounted immediately below the quartz block 32 so that as the lamps 34 are energized, the light therefrom is more evenly distributed by the quartz block 32 over the platform 30 to evenly expose the portion of the recording film 9 on the platform 30. Operating arms 37—37 extend down from the quartz block 32 into a pressure responsive switch means 38 which, when a given pressure is applied to the platform 30, which depresses the same a given distance against the restraining force of the springs 36—36 a given amount, the switch means will effect a momentary energization of the Xenon lamps 34. By setting the amount of pressure which closes the pressure responsive switch means 38 to one producing an optimum value for the particular type of tissue involved, the machine automatically provides optimum imaging for the particular fingerprinting, medical diagnostic or research or other purpose involve.

As shown in FIG. 9, the recording film 9 is initially wound on a supply reel 40, and an unwound portion of the strip of recording film then passes respectively over and beneath idler rollers 42 and 44, over the platform 30, and under an idler roller 46. The recording film then passes over a resilient guiding leaf 49, extending from a quartz block 47 spring-urged upwardly by springs 48—48, and between a transparent plate 50 and the quartz block 47 at the viewing station 28. A florescent or incandescent light source 52 is shown mounted immediately below the quartz block 47 so that when the light source 52 is energized light will be passed through the quartz block to evenly back-light the film which passes between the quartz block 47 and the transparent plate 50. The force of the springs 48—48 presses the quartz block 47 against the recording film 9 thereabove, which in turn is pressed against the bottom surface of the transparent viewing plate 50.

After leaving the viewing station the recording film 9 passes over another guiding leaf 49 and then under idler roller 55 and over an idler roller 57, where the recording film then extends downwardly around a take-up reel 59. The take-up reel 59 is driven from a suitable motor 61, the energization of which is controlled by a control circuit 63, which is a circuit which responds to the pressure responsive switch means 38 in a manner to be explained.

The machine 19 is energized from a suitable source of AC voltage. A power on-off switch 65 controls the feeding of the AC power to the apparatus described. To this end an AC input line connects to the switch 65, in turn, connected to control circuit 63 and a DC power supply 42 which produces a DC voltage from the AC input voltage to energize the control circuit 63. When the pressure responsive switch means 38 is operated by a given degree of pressure applied against the raised platform 30, the control circuit becomes operative to couple momentarily the source of AC power to the Xenon flash lamps 34. Also, after momentary energization of the lamps 34, the control circuit 63 then momentarily energizes the motor 61 for a sufficient time to drive the take-up reel 59 an amount which will bring the section of the recording film 9 just exposed opposite the viewing station 28, where the image for ed thereon can be viewed. The lamp 52 at the viewing station 28 is shown energized from the AC line 66. (Obviously, another line not shown, from the AC source involved is provided to complete an energization circuit to the lamps 52 and 34, and the power supply 42.)

To identify the person or specimen whose surface topology record appears in each exposed frame of the roll of recording film 9, there may be placed face-down on the platform 30 as each tissue specimen is applied thereto a strip preferably with raised or depressed characters identifying the person or specimen involved. The strip may be designed to produce an image of the characters thereon in the same way the tissue produces an image, namely by their differential heat-sinking effect. In the alternative, identifying indicia may be produced directly upon the recording film at the specimen station by optically projecting an image onto the imaging layer from either side of platform 30 which image identified the person or the specimen involved, or an image can be produced from the imaging layer side of the recording film by utilizing the heat-generating character imprinting recording head disclosed in co-pending application Ser. No. 871,935, filed Jan. 23, 1978. The application of the speciman identifying information on the recording film could be carried out at a point other than the specimen station illustrated in FIGS. 9 and 10, since the dry process recording film involved is an "add-on" type of film where only portions of the film exposed to imaging energy are affected, and so areas of the recording film to receive specimen identifying information can be masked from the imaging energy supplied at the specimen station for surface imaging.

It should be apparent that the invention provides a unique method and apparatus which can produce immediately upon exposure of the recording film with a flash of electromagnetic energy a very clear, high resolution, transparency record of the surface topology of live skin or other tissue. Also, the flash of electromagnetic energy in the imaging process produces no pain or discomfort in the skin of those persons whose skin surface topology is recorded by the invention. Moreover, the image record obtained is a permanent one, which does not require any special temperature or moisture conditions for long-time storage.

We claim:

1. A recording system for recording the surface topology of a given surface, said recording system comprising a platform transparent to electromagnetic energy; a recording film extending over one side of said platform which recording film comprises an electromagnetic imaging energy transparent substrate upon only one side of which is deposited a thin, solid, high optical density film of dispersion imaging material which, upon application of electromagnetic energy to a given point thereof for a given momentary period and in an amount which produces undissipated heat in the imaging material of a certain critical value changes at such point to a fluid state in which the surface tension of the imaging material acts to cause the substantially opaque film to disperse and change to a discontinuous film comprising light-passing openings and deformed material which are frozen in place after termination of electromagnetic energy, the substrate side of the recording film facing said platform; a source of said electromagnetic energy on the other side of said platform for directing said energy through said transparent platform and substrate of said recording film upon said body of imaging material; and means for selectively causing said source of energy of said amount to be directed said given momentary period through said platform into said recording film, the application of a surface to be recorded upon the outer imaging material containing side of said recording film during the entire period said energy is applied thereto having a heat-sinking effect on said recording film, where the projecting portions of said surface will dissipate the heat generated at the points involved in said body of imaging material by said amount of electromagnetic energy, to reduce the undissipated heat energy therein below said critical value which will cause the imaging material to disperse.

2. The recording system of claim 1 wherein there is means responsive to a given pressure on said platform for momentarily causing said source of electromagnetic energy to be directed through said platform.

3. The recording system of claim 1 wherein the spacing between the outer side of the recording film against which said surface is applied and said thin film of imaging material is no greater than about 10 micron.

4. The recording system of claim 1 wherein said thin film of imaging material of the recording film has a thickness substantially less than 1 micron.

5. a recording system for recording the surface topology of a given surface, said recording system comprising a platform transparent to electromagnetic energy; a recording film extending over one side of said platform which recording film comprises an electromagnetic imaging energy transparent substrate upon only one side of which is deposited a thin, solid film of an imaging material which, upon application of said electromagnetic imaging energy thereto for a given momentary period in an amount which, in the absence of any heat dissipating surface contiguous to said side of the recording film, produces heat in the imaging material of a certain critical value, has the optical density thereof modified to produce an image thereon which remains after termination of said energy, the substrate side of the recording film facing said platform; a source of said electromagnetic imaging energy on the other side of said platform for directing electromagnetic imaging energy through said transparent platform and substrate of said recording film for said given momentary period upon said body of imaging material; and means for causing said source of energy of said amount to be directed momentarily through said platform into said recording film, the application of a surface to be recorded upon the outer imaging material containing side of said recording film having a heat-sinking effect on said recording film, where the projecting portions of said surface will dissipate the heat generated at the points involved in said body of imaging material by said amount of electromagnetic energy, to reduce the undissipated heat energy therein below said critical value which will cause the imaging material to be modified thereby.

6. The recording system of claim 5 wherein there is provided means responsive to a given pressure on said platform by momentarily causing said source of electromagnetic energy to be directed through said platform.

7. A recording system for recording the surface topology of a given surface, said recording system comprising: a recording film supported to receive on an exposed side thereof the surface of a body whose surface topology is to be recorded, said recording film including an imaging energy transparent substrate upon only one side of which is deposited a thin, solid film of an imaging material which, upon application of said imaging energy thereto for a given momentary period in an amount which, in the absence of any heat dissipating surface contiguous to said side of the recording film, produces heat in the imaging material of a certain critical value, has the optical density thereof modified to produce an image thereon which remains after termination of said energy, said exposed side of the recording film being the side thereof where said imaging material is deposited; a source of said imaging energy on the other side of said recording film; means for causing said source of imaging energy of said amount to be directed for said given momentary period through said substrate into said deposited imaging material, the application of a surface to be recorded upon the exposed imaging material deposited side of said recording film having a heat-sinking effect on said recording film, where the projecting portions of said surface will dissipate the heat generated at the points involved in said film of imaging material by said amount of energy, to reduce the undissipated heat energy therein below said critical value which will cause the imaging material to disperse; and means responsive to a given pressure of the surface whose topology is to be recorded on said film for causing said source of energy to be directed through said platform for said given momentary period.

8. The recording system of claim 7 wherein the spacing between the exposed side of the recording film against which said surface is applied and said thin film of imaging material is no greater than about 10 micron.

9. The recording system of claim 7 wherein said film of imaging material of the recording film has a thickness substantially less than 1 micron.

10. The recording system of claim 7 wherein there is a thin protective overcoat layer on said imaging material of said recording film to protect the imaging material from abrasion.

11. The recording system of claim 7 wherein there is a protective overcoat layer over said imaging material of said recording film which layer is no greater than about 1 micron thick.

12. The recording system of claim 1, 5 or 7 wherein said film of imaging material of said recording film has a thickness no greater than about 0.1 micron.

13. The recording system of claim 7 wherein said recording film comprises an electromagnetic imaging energy transparent substrate upon only one side of which is deposited a thin, solid, high optical density film of a dispersion imaging material which, upon application of said imaging energy thereto in an amount which in the absence of any heat dissipating surface contiguous to said side of the recording film produces heat in the imaging material of a certain critical value, is changed to a fluid state in which the surface tension of the imaging material acts to cause the substantially opaque film to disperse and change to a discontinuous film comprising light-passing openings and deformed material which are frozen in place after termination of said energy.

14. The recording system of claim 1, 5 or 7 wherein said given momentary period during which said electromagnetic energy is applied to said recording film is no greater than about 1/1000 of a second.

15. The recording system of claim 1, 5 or 7 wherein said given momentary period during which said electromagnetic energy is applied to said recording film is no greater than about 1/10,000 of a second.

* * * * *

UNITED STATES PATENT AND TRADEMARK OFFICE
CERTIFICATE OF CORRECTION

PATENT NO. : 4,404,926

DATED : Sept. 20, 1983

INVENTOR(S) : M. McCormick-Goodhart et al.

It is certified that error appears in the above-identified patent and that said Letters Patent is hereby corrected as shown below:

```
     Column 2, line 13, after "free" insert --space--.
     Column 5, line 27, delete "of" and insert --to--.
     Column 7, line 42, delete "spaced" and insert
--spaces--.
     Column 8, line 48, after "spring-urged" insert --,--.
     Column 9, line 1, delete "topole" and insert
--topology--.
     Column 10, line 11, delete "tranparent" and insert --
transparent--.
     Column 10, line 12, delete the words "refer red" and
insert --referred--.
     Column 10, line 48, delete "micro" and insert
--micron--.
     Column 11, line 10, after "14f," insert --14g,--.
     Column 11, line 18, delete "globule" and insert
--globules--.
     Column 11, line 22, after --11c-- insert --,--.
     Column 11, line 46, after "film" insert --is--.
     Column 11, line 52, after "effect" insert --.--.
```

UNITED STATES PATENT AND TRADEMARK OFFICE
CERTIFICATE OF CORRECTION

PATENT NO. : 4,404,926  Page 2 of 2
DATED : Sept. 20, 1983
INVENTOR(S) : M. McCormick-Goodhart et al.

It is certified that error appears in the above-identified patent and that said Letters Patent is hereby corrected as shown below:

Column 11, line 54, delete "finish" and insert --fine--.
    Column 14, line 14, delete "with out" and insert --without--.
    Column 14, line 57, delete "resistan" and insert --resistance--.
    Column 15, line 65, delete "an" and insert --and--.
    Column 15, line 66, delete "th".
    Column 15, line 67, delete "are the" and after "oxide" insert --is--.
    Column 16, line 31, delete "involve" and insert --involved--.
    Column 17, line 7, delete "for ed" and insert --formed--.
    Column 17, line 31, delete "speciman" and insert --specimen--.
    Column 18, line 27, delete "micron" and insert --microns--.
    Column 19, line 37, delete "micron" and insert --microns--.

Signed and Sealed this

Sixteenth Day of April 1985

[SEAL]

Attest:

DONALD J. QUIGG

Attesting Officer  Acting Commissioner of Patents and Trademarks